United States Patent [19]

Fabiani et al.

[11] 4,353,903
[45] Oct. 12, 1982

[54] 2,3-DIHYDRO-IMIDAZO[1,2-b]PYRIDAZINE DERIVATIVES, THEIR PREPARATION AND USE IN TREATMENT OF DEPRESSION

[75] Inventors: Paul Fabiani, Neuilly; Francis Rose, Paris; Abkar Vartanian, Amilly; Christian Warolin, Paris, all of France

[73] Assignee: Synthelabo, Paris, France

[21] Appl. No.: 225,265

[22] Filed: Jan. 15, 1981

[30] Foreign Application Priority Data

Jan. 16, 1980 [FR] France .................. 80 00926

[51] Int. Cl.³ .................. C07D 487/04; A61K 31/50
[52] U.S. Cl. .................. 424/250; 544/236; 544/238; 544/224
[58] Field of Search .................. 424/250; 544/236

[56] References Cited

U.S. PATENT DOCUMENTS 3,828,041  8/1974  Tomcufcik .................. 544/236

OTHER PUBLICATIONS

Ermoldeva et al., Chem. Abs. 80, 95859a, (1974).
Ostrorasnick et al., Chem Abs. 72, 12684a, (1969).

Primary Examiner—Mark L. Berch
Attorney, Agent, or Firm—Wegner & Bretschneider

[57] ABSTRACT

2,3-Dihydro-imidazo[1,2-b]pyridazine derivatives of the formula:

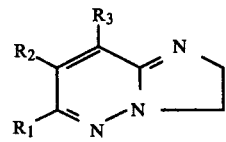

in which $R_1$ represents a phenyl, halogenophenyl, trifluoromethylphenyl, $C_{(1-4)}$-alkylphenyl, $(C_{1-4})$-alkoxyphenyl, hydroxyphenyl, nitrophenyl, aminophenyl, $(C_{1-4})$-alkylaminophenyl, di-$(C_{1-4})$-alkylaminophenyl, acetamidophenyl, thienyl, pyridyl, furyl or nitrofuryl radical, $R_2$ represents a hydrogen atom or a $(C_{1-4})$-alkyl radical, and $R_3$ represents a hydrogen atom or a $(C_{1-4})$-alkyl, phenyl, halogenophenyl, trifluoromethylphenyl, $(C_{1-4})$-alkylphenyl, $(C_{1-4})$-alkoxyphenyl, hydroxyphenyl, nitrophenyl, aminophenyl, $(C_{1-4})$-alkylaminophenyl, di-$(C_{1-4})$-alkylaminophenyl or acetamidophenyl radical, and its addition salts with pharmaceutically acceptable acids are useful in therapy as antidepressants. They may be made by cyclization of compounds of the formula:

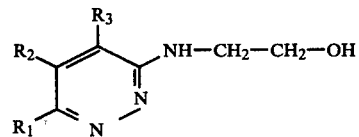

9 Claims, No Drawings

2,3-DIHYDRO-IMIDAZO[1,2-b]PYRIDAZINE DERIVATIVES, THEIR PREPARATION AND USE IN TREATMENT OF DEPRESSION

The present invention relates to 2,3-dihydro-imidazo[1,2-b]pyridazine derivatives, their preparation, and their use.

The compounds of the invention are those of the general formula:

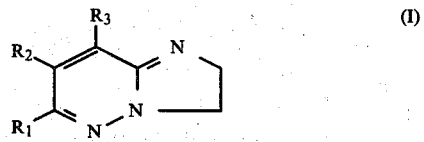

in which $R_1$ represents a phenyl, halogenophenyl, trifluoromethylphenyl, $(C_{1-4})$-alkylphenyl, $(C_{1-4})$-alkoxyphenyl, hydroxyphenyl, aminophenyl, nitrophenyl, $(C_{1-4})$-alkylaminophenyl, di-$(C_{1-4})$-alkylaminophenyl, acetamidophenyl, thienyl, pyridyl, furyl or nitrofuryl radical, $R_2$ represents a hydrogen atom or a $(C_{1-4})$-alkyl radical and $R_3$ represents a hydrogen atom or a $(C_{1-4})$-alkyl, phenyl, halogenophenyl, trifluoromethylphenyl, $(C_{1-4})$-alkylphenyl, $(C_{1-4})$-alkoxyphenyl, hydroxyphenyl, nitrophenyl, aminophenyl, $(C_{1-4})$-alkylaminophenyl, di-$(C_{1-4})$-alkylaminophenyl or acetamidophenyl radical, and their addition salts with pharmaceutically acceptable acids.

Preferred compounds of formula (I) are those in which $R_1$ is an aminophenyl, methylaminophenyl, ethylaminophenyl, dimethylaminophenyl, methoxyphenyl or chlorophenyl radical or a furyl radical, $R_2$ is a hydrogen atom or a methyl radical and $R_3$ is a hydrogen atom or a methyl, phenyl or chlorophenyl radical. More particularly preferred compounds (I) are those in which $R_2$ and $R_3$ each represent a hydrogen atom and $R_1$ represents an aminophenyl, methylaminophenyl, ethylaminophenyl or furyl radical. Where $R_1$ or $R_3$ is a substituted phenyl radical, the substituent is preferably in the p-position.

The compounds of formula (I) may be prepared by cyclisation of a compound of the general formula:

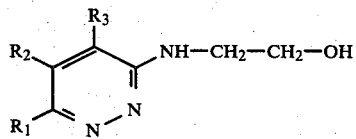

in which $R_1$, $R_2$ and $R_3$ have the abovementioned meanings.

This cyclisation is carried out either by treating the compound of formula (II) with polyphosphoric acid at a temperature of 100° to 250° C., or by treating the compound of formula (II) with thionyl chloride in an inert solvent, such as chloroform, at the reflux temperature and then, after evaporation, heating the residue in ethanol to the reflux temperature in the presence of potassium carbonate or sodium bicarbonate.

The compounds of formula (I) in which $R_1$ represents a dialkylaminophenyl radical can also be prepared by a conventional method of alkylation, starting from the corresponding compound of formula (I) in which $R_1$ is an aminophenyl radical.

The compounds of formula (I) in which $R_1$ represents an acetamidophenyl radical can also be prepared by a conventional method of acetylation, starting from a compound of formula (I) in which $R_1$ is an aminophenyl radical.

The following Examples illustrate the invention. The structure of the new compounds has been confirmed by analyses and by the IR and NMR spectra.

EXAMPLE 1

6-(4-Aminophenyl)-2,3-Dihydro-Imidazo-[1,2-b]Pyridazine and its Hydrochloride

A mixture of 16.1 g (0.07 mol) of 6-(4-aminophenyl)-3-(2-hydroxyethylamino)-pyridazine and 185 g of polyphosphoric acid is heated to 150° C. The temperature is kept between 150° and 160° C. for 30 minutes. The mixture is cooled to about 100° C. and poured into 400 ml of cold water. The solution obtained is cooled in an ice-bath and is rendered alkaline with 400 ml of sodium hydroxide solution (about 10 N). The product which has precipitated is filtered off, washed with water and dried in vacuo. After purification, the base is obtained, m.p. 259° C.

6.5 g (0.03 mol) of this product are dissolved in 350 ml of methanol under reflux. The solution is filtered hot and one equivalent of ethanolic hydrochloric acid is then added. The hydrochloride precipitates. After cooling, the hydrochloride product is filtered off, washed with methanol and dried, m.p. 302°–303° C. (decomposition).

EXAMPLE 2

6-(2-Furyl)-2,3-Dihydro-Imidazo[1,2-b]-Pyridazine and its Hydrochloride 200 ml of chloroform and then 5.5 g (0.0268 mol) of 6-(2-furyl)-3-(2-hydroxyethylamino)-pyridazine are introduced into a 500 ml flask, provided with a magnetic stirrer. 5 ml of thionyl chloride are slowly added in the course of 10 minutes and the mixture is then heated at the reflux temperature for 1½ hours. This results in crystallisation of a cream-coloured product. The mixture is concentrated to dryness in a rotary evaporator, and dissolved in 150 ml of absolute ethanol. The ethanolic solution is heated at the reflux temperature with 10 g of potassium carbonate for one hour, with constant magnetic stirring. The mixture is filtered and the ethanolic solution is concentrated to dryness.

The base is obtained, m.p. 223° C.

This base is taken up in a mixture of 50 ml of ethanol and 20 ml of methanol, and 5 ml of 5 N ethanolic hydrochloric acid are added. The solution is treated while hot with charcoal and filtered hot. The filtrate is then left to cool to ambient temperature, and subsequently left in a refrigerator overnight. The mixture is filtered and the residue is rinsed with alcohol and dried in an oven at 70° C. in vacuo. The hydrochloride is obtained, m.p. 265°–268° C.

EXAMPLE 3

6-(4-Dimethylaminophenyl)-2,3-Dihydro-Imidazo[1,2-b]Pyridazine and its Hydrochloride 1.52 g (0.0072 mol) of 6-(4-aminophenyl)-2,3-dihydro-imidazo[1,2-b]pyridazine, prepared as described in Example 1, are introduced into a 100 ml flask provided with a magnetic stirrer. 6.2 ml of 37% strength aqueous formaldehyde are added. When solution is complete, 1.37 g (0.0232 mol) of sodium cyanoborohydride are added, followed by 0.77 ml of acetic acid dropwise in the course of 7 minutes. The temperature of the medium rises. The mixture is stirred for two hours. 0.77 ml of acetic acid are then added and the mixture is stirred for a further hour. It is then evaporated to dryness in a rotary evaporator, and the residue is taken up in 50 ml of chloroform. The chloroform mixture is washed with 50 ml of 1 N sodium hydroxide solution and then with water (2×50 ml). The product is extracted with 50 ml of 1 N hydrochloric acid and the extract is washed with 50 ml of chloroform. The aqueous phase is rendered alkaline with 1 N sodium hydroxide solution. The precipitate is filtered off, washed with water and dried. 1.6 g of the base obtained are dissolved in 50 ml of warm ethanol, and one equivalent of hydrochloric acid in ethanol and then 75 ml of diethyl ether are added. The precipitate is filtered off and dried, m.p. 259°–261° C.

The compounds of the invention which have been prepared by way of examples are shown in Table I which follows.

TABLE I

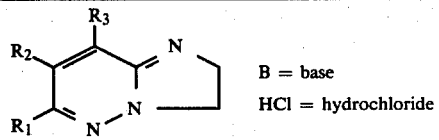

B = base
HCl = hydrochloride

| No. | R₁ | R₂ | R₃ | Base or salt | Melting point (°C.) |
| --- | --- | --- | --- | --- | --- |
| 1 | C₆H₅– | H | H | HCl | 265–6 |
| 2 | Cl–C₆H₄– | H | H | HCl | 255–7 |
| 3 (Example 1) | H₂N–C₆H₄– | H | H | HCl | 302–3 (decomposition) |
| 4 | CH₃O–C₆H₄– | H | H | HCl | 245–7 |
| 5 | CH₃–C₆H₄– | H | H | HCl | 255–60 |
| 6 | HO–C₆H₄– | H | H | B | 270–2 |
| 7 | 3-NO₂–C₆H₄– | H | H | HCl | 275–7 |
| 8 | F₃C–C₆H₄– | H | H | HCl | 250–2 |
| 9 | 3-CF₃–C₆H₄– | H | H | HCl | 256 |
| 10 | 3-NH₂–C₆H₄– | H | H | HCl | 295–7 (decomposition) |
| 11 | CH₃NH–C₆H₄– | H | H | HCl | 292–4 |
| 12 (Example 3) | (CH₃)₂N–C₆H₄– | H | H | HCl | 259–61 |

TABLE I-continued
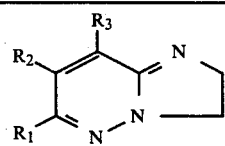
B = base
HCl = hydrochloride
| No. | R₁ | R₂ | R₃ | Base or salt | Melting point (°C.) |
|---|---|---|---|---|---|
| 13 | CH₃—C(=O)—NH—C₆H₄— | H | H | HCl | 296–7 |
| 14 | C₂H₅—NH—C₆H₄— | H | H | HCl | 243–4 |
| 15 | nC₃H₇—NH—C₆H₄— | H | H | HCl | 230–2 |
| 16 | 2-thienyl | H | H | HCl | 268–70 (decomposition) |
| 17 | 4-pyridyl | H | H | HCl | 285–90 (decomposition) |
| 18 | 2-furyl | H | H | HCl | 265–8 |
| (Example 2) | | | | | |
| 19 | C₆H₅— | H | C₆H₅— | HCl / B | 286–8 / 145 |
| 20 | C₆H₅— | H | 3-Cl-C₆H₄— | HCl | 242–4 |
| 21 | C₆H₅— | H | 4-Cl-C₆H₄— | B | 144 |
| 22 | C₆H₅— | H | 2-Cl-C₆H₄— | B | 143 |
| 23 | 3-Cl-C₆H₄— | H | C₆H₅— | HCl | 223–7 |
| 24 | 2-Cl-C₆H₄— | H | C₆H₅— | HCl | 261–3 |
| 25 | 4-Cl-C₆H₄— | H | C₆H₅— | HCl | 253–5 |
| 26 | 3-CF₃-C₆H₄— | H | C₆H₅— | HCl | 254–5 |

TABLE I-continued $$R_2 \underset{R_1}{\overset{R_3}{\diagdown}} \underset{N}{\diagdown} \underset{N}{\diagdown} \underset{N}{\diagdown}$$

B = base
HCl = hydrochloride

| No. | R₁ | R₂ | R₃ | Base or salt | Melting point (°C.) |
|---|---|---|---|---|---|
| 27 | phenyl | H | CH₃ | HCl | 250 |
| 28 | phenyl | H | C₂H₅ | HCl | 233–5 |
| 29 | phenyl | CH₃ | H | HCl | 235 |
| 30 | 3-Cl-phenyl | H | CH₃ | HCl | 240–1 |
| 31 | 4-Cl-phenyl | H | CH₃ | HCl | 310–2 |
| 32 | 4-CH₃O-phenyl | H | CH₃ | HCl | 250 |
| 33 | 4-HO-phenyl | H | CH₃ | HCl | 328–30 |
| 34 | 4-CH₃-phenyl | H | CH₃ | HCl | 348 |
| 35 | 5-O₂N-furyl | H | H | HCl | 284–6 (dec.) |

In pharmacological tests, the compounds of the invention have demonstrated antidepressant properties.

The toxicity of the new compounds has been determined by intravenous administration to mice. The $LD_{50}$ is generally in the range of 50 to 60 mg/kg.

The antidepressant activity was determined by their antagonism to reserpine-induced ptosis.

Mice (male, strain CD1 Charles River, France, weighing 18–22 g each) simultaneously receive the compound under test or the solvent only (by *intraperitoneal administration*), and reserpine (4 mg/kg, by *subcutaneous administration*). Sixty minutes later, the degree of palpebral ptosis in each mouse is evaluated according to a scale of ratings (from 0 to 4). The average rating and the percentage variation in comparison with the control group are calculated for each dose. The ED 50, or the dose which reduces the average ptosis rating by 50%, compared with the controls, is determined graphically for each compound tested. The ED 50 for intraperitoneal administration varies from 0.05 to 1 mg/kg.

The results of the pharmacological tests show that the compounds of the invention can be used, in human therapy, for treating depression.

The compounds of the invention can be formulated in any form appropriate for oral, parenteral or endorectal administration, for example in the form of tablets, dragees, gelatin-coated pills, potable or injectable solutions, and the like, with any appropriate pharmaceutical carrier or excipient. The oral daily dose can range from 50 to 500 mg., in the case of an adult.

We claim:

1. A compound of the formula:

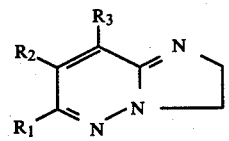

in which $R_1$ represents a phenyl, halogenophenyl, trifluoromethylphenyl, ($C_{1-4}$)-alkylphenyl, ($C_{1-4}$)-alkoxyphenyl, hydroxyphenyl, nitrophenyl, aminophenyl, ($C_{1-4}$)-alkylaminophenyl, di-($C_{1-4}$)-alkylaminophenyl, acetamidophenyl, thienyl, pyridyl, furyl or nitrofuryl radical, $R_2$ represents a hydrogen atom or a ($C_{1-4}$)-alkyl radical, and $R_3$ represents a hydrogen atom or a ($C_{1-4}$)-alkyl, phenyl, halogenophenyl, trifluoromethylphenyl, ($C_{1-4}$)-alkylphenyl, ($C_{1-4}$)-alkoxyphenyl, hydroxyphenyl, nitrophenyl, aminophenyl, ($C_{1-4}$)-alkylaminophenyl, di-($C_{1-4}$)-alkyl-aminophenyl or acetamidophenyl radical, and its addition salts with pharmaceutically acceptable acids.

2. A compound according to claim 1, in which $R_1$ represents a phenyl, chlorophenyl, trifluoromethylphenyl, methylphenyl, methoxyphenyl, hydroxyphenyl, nitrophenyl, aminophenyl, methylaminophenyl, ethylaminophenyl, propylaminophenyl, dimethylaminophenyl, acetamidophenyl, thienyl, pyridyl or furyl radical, $R_2$ represents a hydrogen atom or a $(C_{1-4})$-alkyl radical, and $R_3$ represents a hydrogen atom or a $(C_{1-4})$-alkyl, phenyl or halogenophenyl radical.

3. A compound according to claim 2, in which $R_1$ is an aminophenyl, methylaminophenyl, ethylaminophenyl, dimethylaminophenyl, methoxyphenyl, chlorophenyl or furyl radical, $R_2$ is a hydrogen atom or a methyl radical, and $R_3$ is a hydrogen atom or a methyl, phenyl or chlorophenyl radical.

4. A compound according to claim 3, in which $R_1$ is an aminophenyl, methylaminophenyl, ethylaminophenyl or furyl radical, and $R_2$ and $R_3$ are each a hydrogen atom.

5. 6-(4-Aminophenyl)-2,3-dihydro-imidazo[1,2-b]pyridazine and its pharmaceutically acceptable acid addition salts.

6. 6-(4-Methylaminophenyl)-2,3-dihydro-imidazo[1,2-b]pyridazine and its pharmaceutically acceptable acid addition salts.

7. 6-(2,Furyl)-2,3-dihydro-imidazo[1,2-b]pyridazine and its pharmaceutically acceptable acid addition salts.

8. A pharmaceutical composition for the treatment of depression comprising an anti-depression effective amount of a compound as claimed in claim 1 in association with a pharmaceutical carrier.

9. Method of treating depression which comprises administering to a patient subject thereto an effective amount of a composition as claimed in claim 8.

* * * * *